US010679200B1

(12) United States Patent
Wolter

(10) Patent No.: US 10,679,200 B1
(45) Date of Patent: Jun. 9, 2020

(54) VIDEO ANALYSIS OF FOOD SERVICE COUNTER OPERATIONS

(71) Applicant: Square, Inc., San Francisco, CA (US)

(72) Inventor: Jonathan Andrew Wolter, San Francisco, CA (US)

(73) Assignee: Square, Inc., San Francisco, CA (US)

( * ) Notice: Subject to any disclaimer, the term of this patent is extended or adjusted under 35 U.S.C. 154(b) by 595 days.

(21) Appl. No.: 15/382,110

(22) Filed: Dec. 16, 2016

(51) Int. Cl.
| G06Q 10/00 | (2012.01) |
| G06Q 20/20 | (2012.01) |
| G06Q 10/08 | (2012.01) |
| G06Q 30/02 | (2012.01) |
| G06K 9/00 | (2006.01) |
| G06Q 50/12 | (2012.01) |

(52) U.S. Cl.
CPC ....... *G06Q 20/202* (2013.01); *G06K 9/00711* (2013.01); *G06Q 10/0875* (2013.01); *G06Q 30/0201* (2013.01); *G06Q 30/0282* (2013.01); *G06K 2209/17* (2013.01); *G06Q 50/12* (2013.01)

(58) Field of Classification Search
None
See application file for complete search history.

(56) References Cited

U.S. PATENT DOCUMENTS

| 10,227,226 | B2* | 3/2019 | Jersey | B67D 1/0021 |
| 10,332,053 | B2* | 6/2019 | Herman | G06Q 10/0633 |
| 10,489,868 | B2* | 11/2019 | Long, II | B67D 1/0884 |
| 2005/0160005 | A1* | 7/2005 | Roth | A47F 10/06 705/15 |
| 2005/0211768 | A1* | 9/2005 | Stillman | G07F 11/00 235/381 |
| 2005/0246223 | A1* | 11/2005 | Roth | A47F 10/06 700/231 |
| 2007/0005185 | A1* | 1/2007 | Roth | A47F 10/06 700/231 |
| 2007/0005434 | A1* | 1/2007 | Roth | A47F 10/06 705/15 |
| 2007/0294129 | A1* | 12/2007 | Froseth | G06Q 10/08 705/7.32 |
| 2010/0280918 | A1* | 11/2010 | Balent | G06Q 30/0633 705/26.81 |
| 2014/0121810 | A1* | 5/2014 | Jung | G06Q 10/087 700/115 |
| 2014/0121811 | A1* | 5/2014 | Jung | G06Q 10/087 700/115 |

(Continued)

OTHER PUBLICATIONS

The Top Five Digital Health Innovations for Food Tracking and Eating, Jun. 27, 2017, https://medicalfuturist.com/top-5-digital-innovations-for-food-tracking-and-healthy-eating, p. 1-7.*

*Primary Examiner* — Joseph M Waesco
(74) *Attorney, Agent, or Firm* — Lee & Hayes, P.C.

(57) ABSTRACT

In a restaurant having a customer-facing food service counter, a video camera is positioned to produce video of an area that includes the food service counter. The video is analyzed to determine the ingredients that are used to prepare each of multiple customer meals. This information may be used to recommend a modified ingredient layout of the food service counter, where the modified ingredient layout is formulated so as to improve serving efficiency or customer convenience.

24 Claims, 9 Drawing Sheets

(56) References Cited

U.S. PATENT DOCUMENTS

| | | | |
|---|---|---|---|
| 2014/0122169 A1* | 5/2014 | Jung | G06Q 30/0201 |
| | | | 705/7.29 |
| 2014/0122260 A1* | 5/2014 | Jung | G06Q 50/12 |
| | | | 705/15 |
| 2014/0122261 A1* | 5/2014 | Jung | G06Q 50/12 |
| | | | 705/15 |
| 2015/0120509 A1* | 4/2015 | Moring | G06Q 30/0633 |
| | | | 705/26.81 |
| 2016/0232624 A1* | 8/2016 | Goldberg | G06Q 30/02 |
| 2017/0024790 A1* | 1/2017 | Maggio | G06Q 30/0621 |
| 2017/0293984 A1* | 10/2017 | Goldberg | G06Q 30/02 |
| 2017/0365017 A1* | 12/2017 | Ells | G06Q 20/3278 |
| 2018/0121961 A1* | 5/2018 | Villanueva | G06Q 30/0264 |
| 2018/0232689 A1* | 8/2018 | Minvielle | G06Q 10/087 |

\* cited by examiner

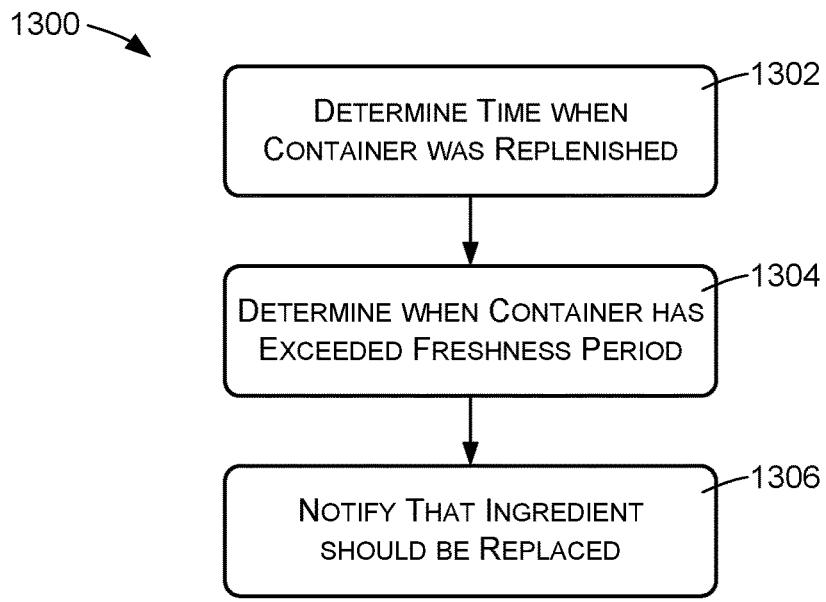
FIG. 13
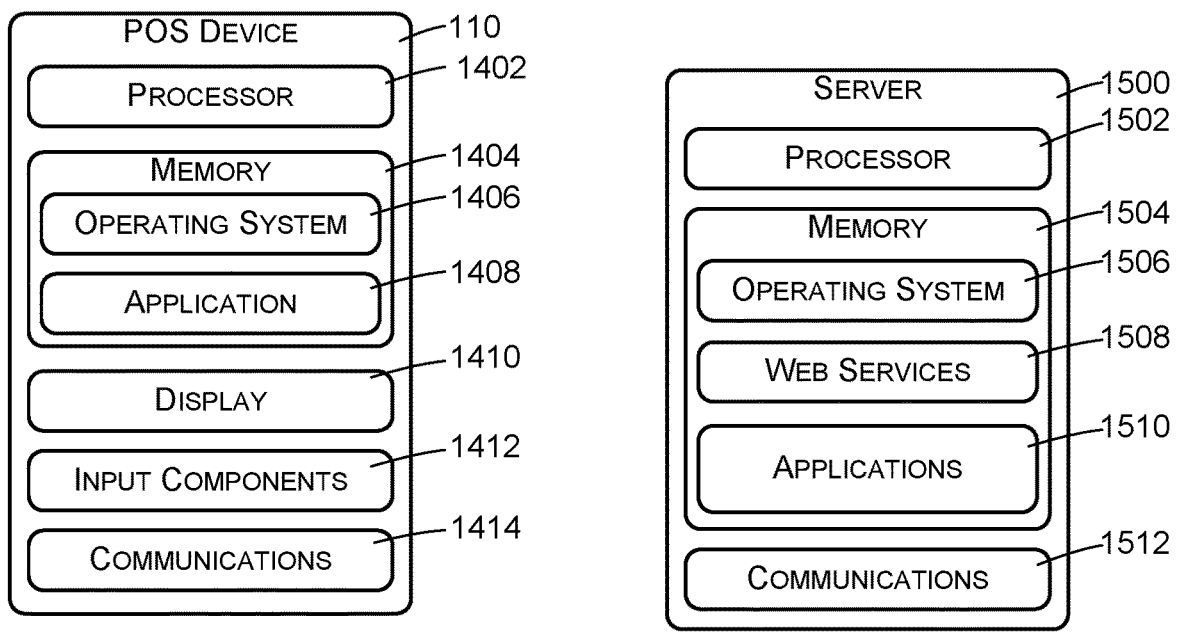
FIG. 14
FIG. 15

VIDEO ANALYSIS OF FOOD SERVICE COUNTER OPERATIONS

BACKGROUND

Certain types of restaurants prepare food from customer-facing production lines while accepting verbal instructions from customers. For example, a customer may order a menu item such as a "Beef Sandwich," which can then be customized with various ingredients. For example, while a Beef Sandwich may always include bread and beef, the type of bread may vary and the sandwich may also include ingredients selected by the customer, such as lettuce, onions, different types of sauces, tomatoes, etc. Some restaurants have food servers, who add the selected ingredients from containers of a food service counter in response to real-time customer instructions. Other restaurants may allow the customers to serve themselves from a food service counter.

Restaurants such as these may utilize one or more online merchant support services for various purposes, such as for order entry, payment processing, table reservations, inventory management, payroll, general accounting, supplies ordering, and so forth.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

FIG. 13 is a flow diagram illustrating an example method of providing notifications that certain ingredients are no longer fresh and should be replaced.

FIG. 14 is a block diagram of an example POS device.

FIG. 15 is a block diagram of an example server computer.

DETAILED DESCRIPTION

Figure 1:
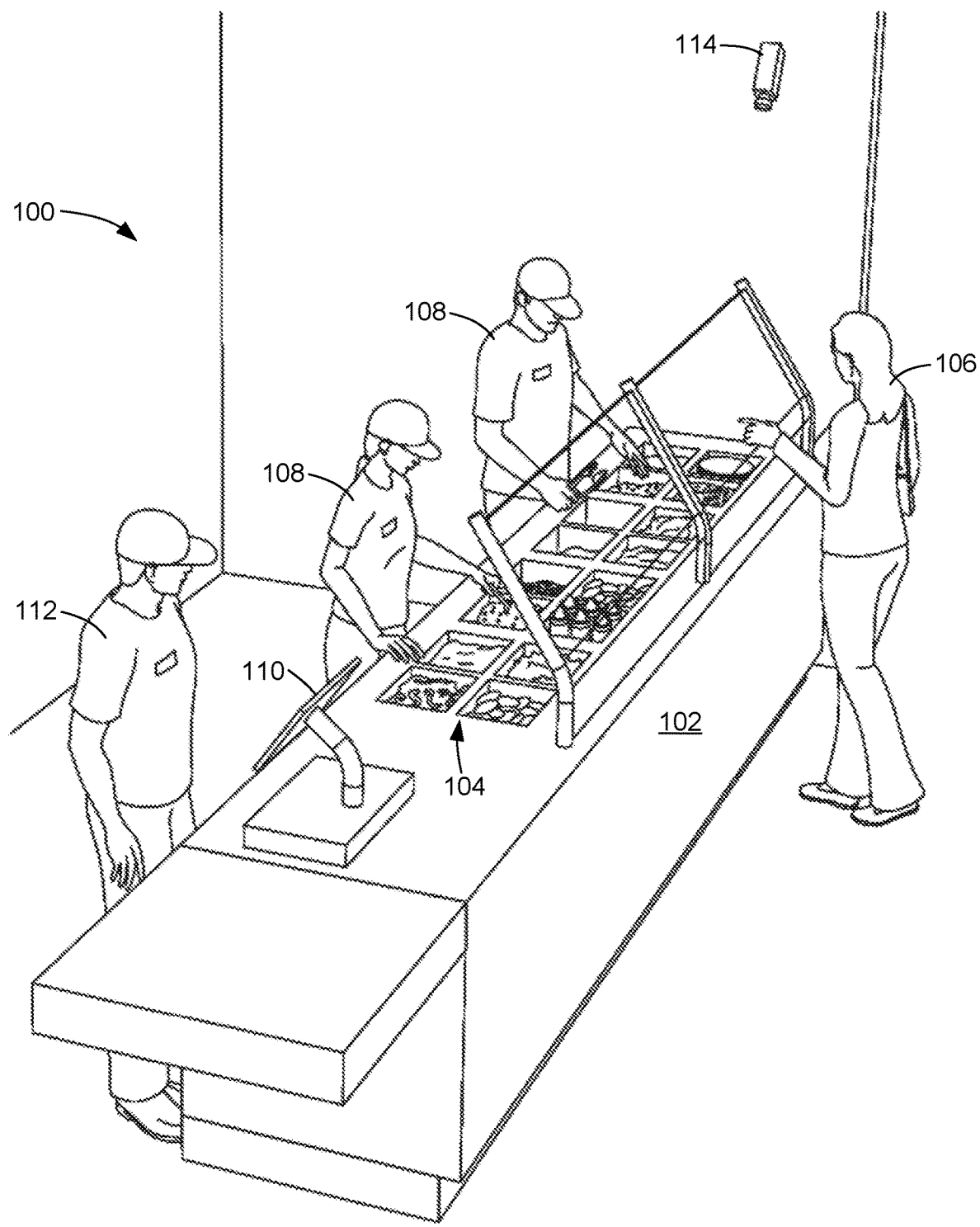
FIG. 1 is a view of a restaurant environment having a food assembly line that includes a food service counter.

Described herein are systems and techniques for obtaining and leveraging information regarding food assembly lines such as are used in certain types of restaurants. The systems and techniques may be particularly useful in restaurants having customer-facing food service counters from which various ingredients are selected by customers in order to prepare a meal. The systems and techniques are applicable in situations in which menu items are prepared from a food service counter by employees of the restaurant, referred to as food servers. The systems and techniques may also be applicable in situations in which customers serve themselves from accessible food service counters.

A food service counter has multiple ingredient containers that hold available ingredients for viewing and selection by a customer. When preparing a meal, a restaurant employee (referred to herein as a "food server") or the customer accesses individual ingredient containers to withdraw ingredients. Typically, each customer selects a combination of food items, which are combined to create a customer meal. For example, multiple ingredients may be selected and used to create a sandwich. The meal is assembled either by the customer or by one or more food servers as the customer watches and instructs. After the meal has been assembled, the customer moves to a check-out position and pays for the meal.

In certain embodiments, customer check-out may be performed using a point-of-sale (POS) device that is supported by an online merchant support service. The merchant support service may provide various services for the restaurant, such as order entry, check-out support, credit-card payment processing, accounting, inventory management, employee time scheduling, payroll, and/or other services.

In the described embodiments, the merchant support service also supports video analysis of food service counter operations. A video camera is placed above the food service counter to produce video of an area that includes the ingredient containers of the food service counter. In certain embodiments, the video camera may be connected to the POS device of the restaurant and may provide the video to the POS device. The POS device may in turn provide the video to the merchant support service using wide-area network (WAN) communications such as the Internet.

The merchant support service performs automated analysis of the video to collect various information about operations of the food service counter and uses the collected information to provide reports to the restaurant through the POS device and/or through other devices used by the restaurant or its employees.

As an example, the merchant support service may analyze the video to identify the ingredients that are selected for each meal assembled from the food service counter. Specifically, the video may be analyzed to detect when each ingredient container is accessed by either a food server or the customer. Using this information, as well as a counter map previously supplied by the restaurant, the merchant support service determines the ingredients of each prepared meal. When the customer checks out and provides a payment instrument such as a credit card, the merchant support service records the meal and its ingredients as having been purchased by the customer that is associated with the payment instrument.

Over time, the merchant support service gathers meal data for many meals, which have been purchased by many customers. The meal data is then analyzed to provide various types of reports to the restaurant. For example, the meal data may be analyzed to detect the most frequently selected ingredients. Based on this information, the merchant support service may recommend that the ingredient layout of the food service counter be modified in a way that is likely to improve the speed of service. As another example, the merchant support service may provide a report of the most popular ingredient combinations, which the restaurant may use as the basis of new or modified menu items.

The meal data may also be used in real time for certain purposes. For example, the meal data may indicate how much of a particular ingredient has been used since that ingredient was last replenished. Based on this information, the merchant support service may determine when it is time for a particular ingredient to be replenished, and may notify the restaurant of the need to replenish the ingredient at the determined time. In some cases, the merchant support service may provide a notification at an earlier time, at which preparation of the ingredient should begin.

Meal data may also be used to determine how usage rates of different ingredients vary over different time periods, such as by time of day, time of week, or time of year. The merchant support service may provide recommendations regarding preparation activities based on this information, as well as on variances in usage rates that are detected in real time.

In certain embodiments, the merchant support service may analyze the video to identify actions of the food servers while preparing a meal. For example, various types of motions and gestures may be identified and characterized in order to evaluate effectiveness of the food servers. An addition, facial images of the food servers may be evaluated to identify individual food servers and to determine expressions (such as smiles) of food servers. For example, the analysis might reveal whether or not food servers are smiling during customer interactions. Analyses of the actions of the food servers may be performed over time, and recommendations for improvement may be made in general or with regard to individual food servers.

In certain embodiments, the merchant support service may analyze video of customers' faces to evaluate customer satisfaction. In some embodiments, the evaluated customer satisfaction may be correlated with actions of the food servers to learn which food server actions are detrimental to customer satisfaction and to report when such actions occur. In some cases, customers may also provide explicit feedback through various types of feedback mechanisms, and this explicit feedback may similarly be correlated with the actions of the food servers.

Customer faces may also be analyzed to determine demographic information such as gender and age. Demographic information such as this may be collected for each meal, and subsequently analyzed to determine popularity of menu items and food combinations for different demographic groups. Information such as this may be used for advertising and promotional purposes.

FIG. 1 shows an example restaurant environment 100 having a food service counter 102 from which meals are prepared. The food service counter 102 has multiple ingredient containers 104 that hold ingredients for viewing and selection by a customer 106. In some embodiments, the food ingredients are served from the food service counter 102 by one or more food servers 108. In certain environments, the customer 106 may ask for a particular menu item, which might correspond to a type of food item associated with a default set of ingredients. The customer 106 moves along the food service counter 102 and selects different ingredients from the ingredient containers 104. The food servers 108 access the ingredient containers 104 to assemble the requested menu item using the ingredients requested by the customer, resulting in what will be referred to herein as a customer meal. As examples, a menu item might comprise a sandwich, a burrito, or a salad, and the customer may select particular ingredients to be used in one of these menu items. Note that in some environments, the customer 106 may access the ingredient containers 104 to assemble the meal, rather than relying on the food servers 108.

A point-of-sale (POS) device 110 is located at the end of the food service counter 102. The POS device 110 is used by a service person 112 to specify purchased menu items and to accept and process payment from the customer 106. Although only a single POS device 110 is shown in FIG. 1, a given restaurant may have a POS system comprising multiple POS devices at different locations with the restaurant. For example, there may be multiple checkout stations that have respective POS devices 110. Furthermore, such a POS system may include additional devices, having similar functionality, that are located in different locations of the restaurant, such as at food preparation locations, in offices, etc., and may be used for various purposes. The reports described herein may be provided at any of these devices.

A video camera 114 is positioned so that it captures video of an area that includes the ingredient containers 104. For example, the video camera 114 may be positioned above the food service counter 102 as shown in FIG. 1. In some embodiments, the video camera 114 may be positioned to also view the food servers 108 and/or the customer 106. In certain embodiments, multiple video cameras 114 may be positioned relative to the food service counter to capture video of all of the ingredient containers 104, the faces of the food servers 108, and/or the face of the customer 106. Although various techniques are described below in relation to a single video stream, it is to be understood that the techniques may also be used with multiple video streams produced by multiple cameras that are at different positions relative to the food service counter 102 in order to view different objects and actors.

Note that in the following description, a restaurant is considered to be a type of merchant, and the terms "restaurant" and "merchant" are used to refer to people who act on behalf of the restaurant or merchant, such as employees of the restaurant or merchant.

Figure 2:
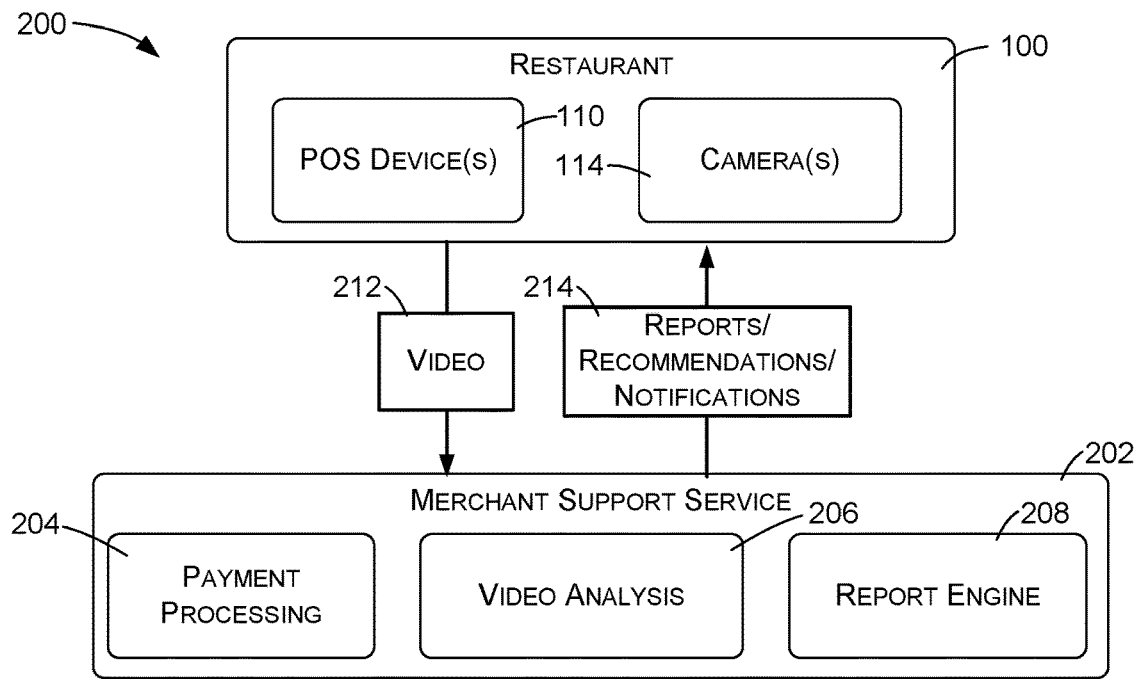
FIG. 2 is a block diagram of an example system for providing reports, recommendations, and/or notifications to a restaurant based on video analysis of a food assembly line.

FIG. 2 shows an example system 200 that includes one or more POS devices 110 and one or more video cameras 114, which as described above are within the restaurant environment 100. For simplicity of discussion, the one or more POS devices 110 and the one or more video cameras 114 will be referred to in the singular.

The POS device 110 may comprise any sort of mobile or non-mobile device having a display or other means for presenting information to restaurant staff and for receiving input from restaurant staff. For example, the POS device may comprise a smartphone or tablet computer having a touch-sensitive graphics display surface that both displays information and receives user input. More generally, the POS device 110 may comprise any of various types of devices, including registers, terminals, desktop computers, laptop computers, mobile computing devices, etc.

The POS device 110 may be supported by an online merchant support service 202 that is accessible via network communications and that is implemented by multiple server computers that run software for providing functionality that is useful to merchants, including restaurants. The merchant support service 202 may in some cases comprise a large-scale service that supports many merchants, who may be distributed across large geographic areas.

The POS device 110 and the merchant support service 202 may be configured to communicate with each other using a wide-area network (WAN) such as the Internet (not shown). Network communications may utilize any one or more wired or wireless networking technologies, such as Ethernet, Wi-Fi, and/or cellular communication technologies. Networks involved in the communications between the POS device 110 and the merchant support service 202 may include private networks as well as public networks, including the Internet.

In combination, the POS device 110 and the merchant support service 202 provide various functionality that may be useful for restaurant operations. In the described embodiments, the merchant support service 202 is responsible for core system functionality. The POS device 110 takes the role of a client that exposes a user interface and that allows for other local input/output functionality such as reading credit cards and displaying reports. However, some embodiments may distribute the functionality of the system 200 in different ways, and the POS device 110 and/or other devices local to the restaurant environment 100 may be responsible for some or all aspects of system functionality.

In certain embodiments, the merchant support service 202 may expose its functionality through pages of a website that are accessed and displayed by the POS device 110, using an Internet browser that runs on the POS device. In other embodiments, the POS device 110 may run a special-purpose client application that is configured to implement and expose POS services in conjunction with the merchant support service 202, using network APIs (application program interfaces) that are made available by the merchant support service 202.

Among various different types of services, the system 200 may provide POS services enabling the restaurant (e.g., an owner, employees, etc.) to accept payments from the customer 106. When paying for a meal or other item, the customer 106 typically offers a payment instrument (e.g., a debit card, a credit card, a stored-value or gift card, a check, through an electronic payment application on a device carried by the customer, or the like). The service person 112 interacts with the POS device 110 to process the payment, such as by inputting (e.g., manually, via a magnetic card reader or an RFID reader, etc.) an identifier associated with the payment instrument. For example, a payment instrument of the customer 106 may include one or more magnetic strips for providing card and customer information when swiped in a card reader. In other examples, other types of payment cards may be used, such as smart cards having built-in memory chips that are read by the POS device 110 when the cards are "dipped" into the reader, radio frequency identification tags, or so forth.

In order to complete a purchase transaction, the POS device 110 determines transaction information describing the transaction, such as the identifier of the payment instrument, an amount of payment to be made by the customer, the items acquired by the customer, etc. The merchant support service 202 receives the transaction information from the POS device 110 and attempts to authorize a payment instrument specified by the transaction information. Upon authorization, the merchant support service 202 sends an indication of whether the payment instrument has been approved or declined back to the POS device 110.

Generally, the merchant support service 202 may have multiple functional components, corresponding to different services that are provided for use by merchants. For example, such components may include a payment processing component 204 that is configured to perform payment transaction processing as described above. Other components relevant to this discussion, and which may in some embodiments be implemented by the merchant support service 202, include a video analysis component 206 and a report engine 208. The merchant support service 202 may in some embodiments implement additional components that are not shown, such as for example a payroll component, an accounting component, a table reservations component, a back-of-house (BOH) management component, an order entry component, and so forth.

The video analysis component 206 of the merchant support service 202 is configured to receive video 212 from the camera 114. In implementation, the camera 114 may be connected as an accessory to the POS device 110. For example, the camera 114 may be connected by a video cable or by a wireless connection to the POS device 110. In such a configuration, the POS device 110 receives video from the camera 114 and provides the video to the video analysis component 206. In other implementations, the camera 114 may communicate directly with the merchant support service 202.

In some cases, the video 212 received by the video analysis component 206 may comprise multiple video streams, from multiple cameras 114 within the restaurant environment 100. Each video stream may comprise a digital video stream formatted in accordance with an appropriate video coding format such as MPEG-4. In the described embodiment, the video is received in real time or near real time, although in other embodiments the video may be stored by the POS device before being provided to the merchant support service 202 at a later time.

The video analysis component 206 analyzes the video 212 to detect actions of the food servers 108 and/or the customer 106. Among other types of actions, the video analysis component 206 determines when and/or how many times the food servers 108 and/or the customer 106 access each ingredient container 104. Such an analysis may use hand recognition techniques, for example, to detect the position of a hand within the received video. When a detected hand pauses or lingers over an ingredient container for a predetermined length of time, the video analysis component 206 may conclude that the hand has accessed the underlying ingredient container 104. Other types of analysis may be used as well to determine when a hand has accessed an ingredient container 104 and therefore has likely withdrawn food from the ingredient container 104.

The report engine 208 analyzes the actions recognized by the video analysis component 206 and provides reports 214, which may include recommendations and/or notifications, to the restaurant, such as to the employees of the restaurant. The reports, recommendations, and/or notifications 214 may be displayed on the POS device 110, for example, or on any other device or devices that are used by restaurant employees such as smartphones or other personal devices of the employees.

Figure 3:
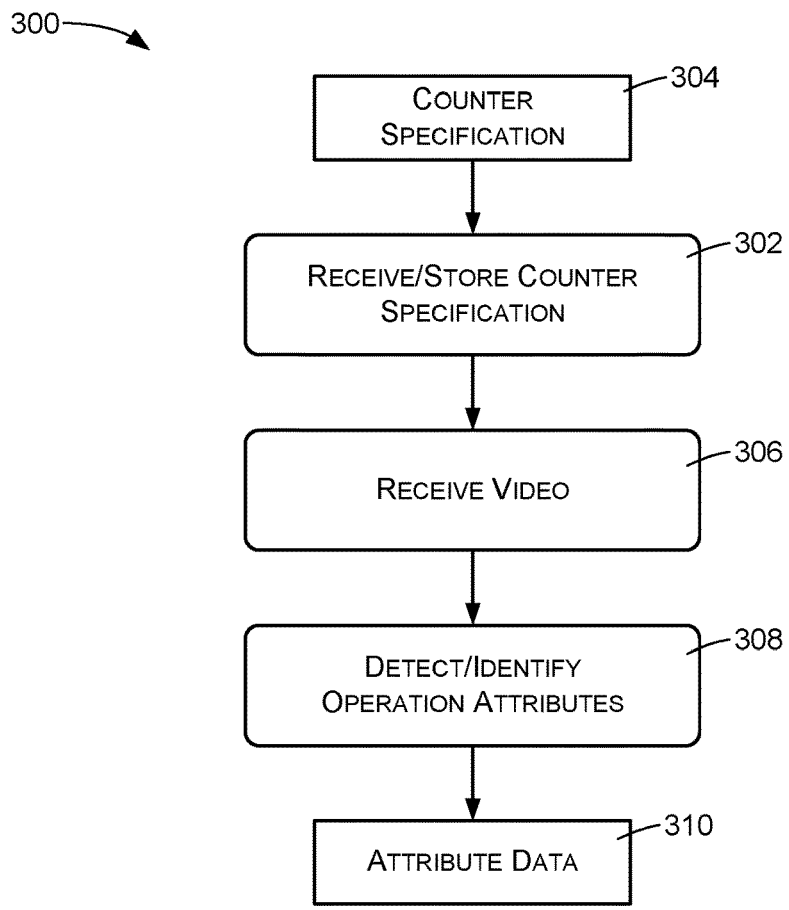
FIG. 3 is a flow diagram illustrating an example method of analyzing video to produce attribute data.

FIG. 3 shows an example method 300 that may be performed by the video analysis component 206 of the merchant support service 202 to detect and characterize aspects of food service line operations. An action 302 comprises receiving and/or storing a counter specification 304 that specifies coordinates of the ingredient containers 104 within the received video 212. In certain embodiments, the video analysis component 206 may rely upon a calibration procedure to establish these coordinates. For example, the merchant support service 202 may show a frame of the received video 212 on the display of the POS device 110 and a restaurant employee may be asked to identify the areas within the frame that represent the ingredient containers 104. For example, the employee may be asked to identify the four corners of each ingredient container 104 within the video frame. This information is stored by the video analysis component 206 for future reference, to delineate between different ingredient containers in the received video 212.

An action 306 comprises receiving the video 212. The video 212 comprises a stream of image frames showing an area within the restaurant environment 100 that includes the food service counter 102. The area may in some embodiments encompass a larger area. For example, the area covered by the video 212 may include an area behind the food service counter 102 that includes the food servers 108 and/or an area in front of the food service counter 102 that includes the customer 106.

An action 308 comprises analyzing the received video 212 to detect and/or identify various attributes relating to operation of the food service counter 102. For purposes of discussion, these attributes are referred to herein as operation attributes. As a specific example, the action 308 may include determining when and/or how many times the food servers 108 and/or the customer 106 access each ingredient container 104.

The detected and/or identified operation attributes are reported to the report/recommendation/notification engine in the form of attribute data 310. In some embodiments, the attribute data 310 specifies each detected or identified operation attribute and the time at which it was detected.

The operation attributes specified by the attribute data 310 may include may include motions, gestures, speech, utterances, and facial expressions of the food servers 108 and the customer 106. For purposes of discussion, detected or identified motions, gestures, speech, utterances, and facial expressions will be referred to herein as observed actions. In some cases, the observed actions may include motions or gestures that correspond to accessing food containers. For each such motion or gesture, the attribute data 310 may specify which of the multiple containers 104 was accessed by the motion or gesture.

In some embodiments, the operation attributes may include demographic information regarding customers. For example, the action 308 may comprise determining one or more demographic attributes of each customer, such as age and/or gender, and the demographic attributes may be specified by the attribute data 310.

In embodiments in which the video 212 includes audio, the action 308 may comprise detecting speech or other utterances of the food servers 108 and/or the customer 106. For example, the video analysis component 206 may include speech-to-text functionality for creating text strings corresponding to utterances of the food servers 108 and/or the customer 106. In these cases, the observed actions specified by the attribute data 310 may include detected speech or utterances and the time at which the speech or utterances occurred.

The action 308 may also include identifying individual food servers among the food servers 108. For example, the action 308 may use facial recognition techniques to identify and distinguish between different food servers 108. Alternatively, the video analysis component 206 may identify the food servers 108 by performing text recognition on nametags or badges worn by the food servers 108. Other means of identifying and distinguishing between the food servers 108 may also be used, such as barcodes, RFID tags, beacons, color coding, etc.

In embodiments in which food server identification is performed, the attribute data 310 may include, for some or all of the observed actions, the identity of the food server 108 who performed each action. As a specific example, the attribute data 310 may indicate, for each motion that corresponds to accessing an ingredient container, the identify of the food server 108 who performed that motion. Similarly, for each other operation attribute attributable to a food server 108, the identity of that food server 108 may be indicated by the attribute data 310.

The report engine 208 analyzes the attribute data 310 to generate and provide the reports, recommendations, and/or notifications 214 through the POS device 110 or other devices within the restaurant environment 100.

Figure 4:
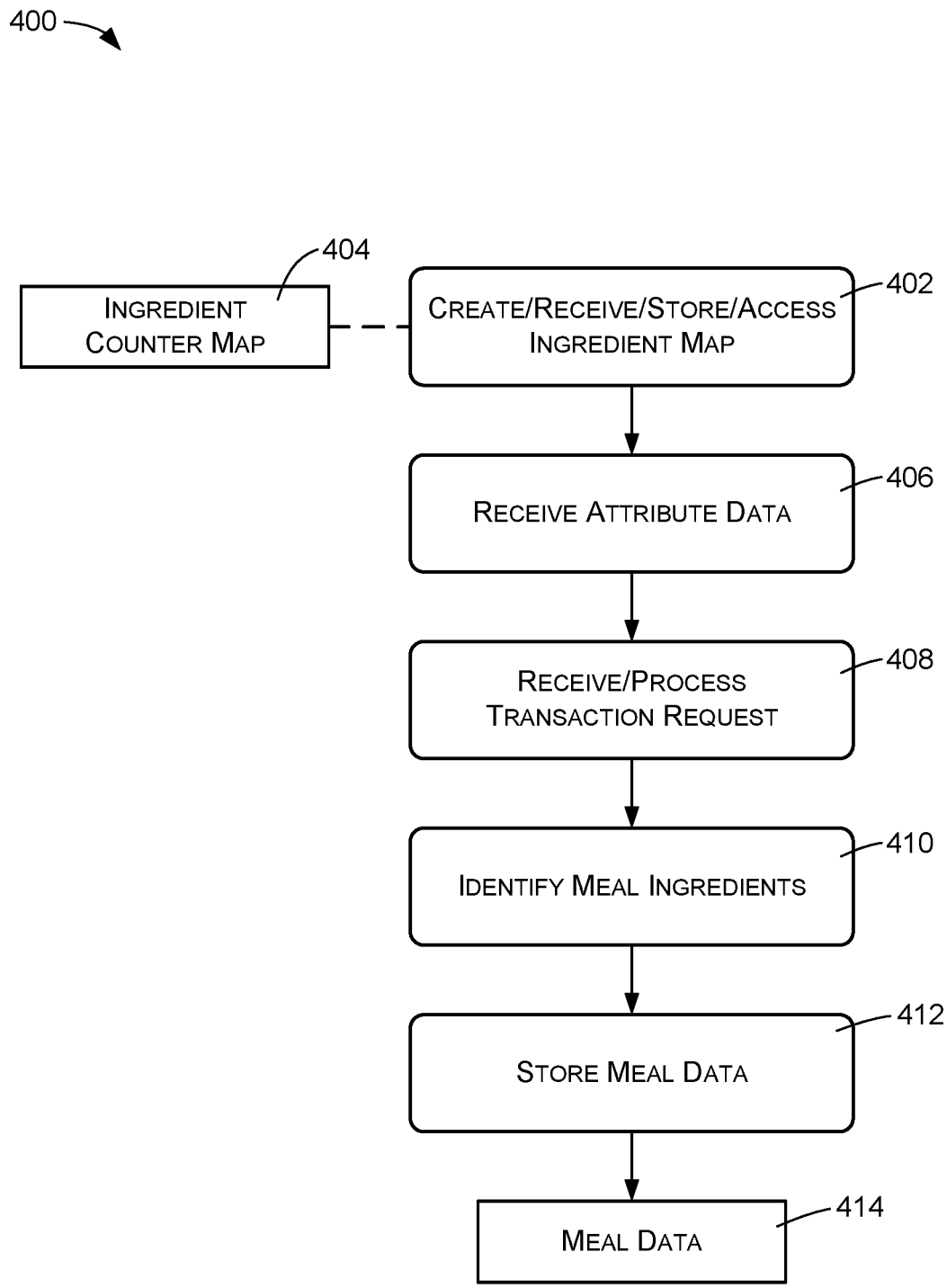
FIG. 4 is a flow diagram illustrating an example method of creating meal data based at least in part on the attribute data.

FIG. 4 shows an example method 400 that may be performed by the merchant support service 202 based at least in part on the actions and/or other operation attributes identified attribute data 310. Parts of the method 400 may in some embodiments be performed by the report engine 208 of the merchant support service 202.

An action 402 comprises creating, receiving, storing, and/or accessing an ingredient counter map 404. The ingredient counter map 404 indicates the ingredient held by each ingredient container 104 of the food service counter 102. As an example, the action 402 may include displaying a representation of the physical layout of the ingredient containers 104 on the POS device 110 and asking a restaurant employee to provide an ingredient name for each container 104. This information is then stored for later use.

An action 406 comprises receiving the attribute data 310 that has been produced by the video analysis component 206 as described above with reference to FIG. 3. The attribute data 310 may be received as a stream, corresponding in time to the times at which operation attributes are detected within the restaurant environment 100. That is, the report engine 208 may receive notifications of actions and other operation attributes as they occur and/or are detected or identified by the video analysis component 206.

An action 408 comprises receiving and/or processing a transaction request, such as a requested generated by the POS device 110 for the purchase of a customer meal. A transaction request, for example, may be received when assembly of a customer meal has been completed and the customer 106 has moved to the check-out position of the food service counter 102. In the described embodiment, the transaction request may be received and processed by the payment processing component 204 of FIG. 2. Information regarding the transaction may also be received by the report engine 208. The transaction information may include an identifier or other information regarding a payment instrument that is being used to pay for the transaction. The transaction information may also indicate a menu item that is being purchased.

An action 410 comprises identifying meal ingredients of the customer meal represented by the transaction processed in the action 406. The action 408 may comprise identifying the ingredient of each ingredient container has been accessed, based the attribute data 310 and the ingredient counter map 404. Specifically, ingredients withdrawn to prepare a customer meal are identified based on which of the ingredient containers 104 were accessed in the time leading up to the transaction request from the POS device 110.

An action 412 comprises compiling and storing meal data 414 for the customer meal represented by the received transaction request. As an example, the action 412 may comprise recording a purchase of the customer meal, including (a) an identifier of the payment instrument used to pay for the customer meal and (b) the identified ingredients of the purchased customer meal.

The meal data 414 may specify data for multiple meals, purchased by multiple customers 106. For each meal, the meal data specifies the particular combination of ingredients that were used to assemble the meal, as identified in the action 410. The meal data 414 may also include an identifier of the menu item for which the customer was charged in the transaction request, and the identifier of the payment instrument used to pay for the meal. Meal data may also include various operation attributes that were detected as the meal was being prepared, such as motions, gestures, and/or facial expressions of the food servers 108 and the customer 106, customer demographic information, etc. The meal data 414 may also indicate identities of food servers 108 who made detected motions, gestures, and/or facial expressions and/or to which the detected operation attributes relate. The meal data 414 may include metadata such as the times corresponding to the operation attributes and the time of each meal purchase.

In cases where the camera 114 has audio capabilities, the meal data may indicate speech or utterances of the food servers 108 and the customer 106 during meal preparation.

In implementations that support post-purchase customer feedback, the customer feedback for a particular meal may be appended meal data 414 for that meal. Accordingly, the meal data 414 for a particular customer meal may include explicit customer feedback relating to the meal and/or to the customer experience while the meal was being prepared.

The meal data 414 is collected and archived for multiple meals as the meals are purchased by different customers 106. Generally, the meal data 414 for a specific customer meal includes the attribute data 310 that corresponds in time to the time during which the customer meal was being prepared, as well as various transaction information relating to the purchase of the customer meal and/or the customer 106 who purchased the customer meal. In some cases, the meal data 414 may also include additional data that has been generated and appended after analyzing the attribute data 310, as well as information such as customer feedback that is subsequently received.

Figure 5:
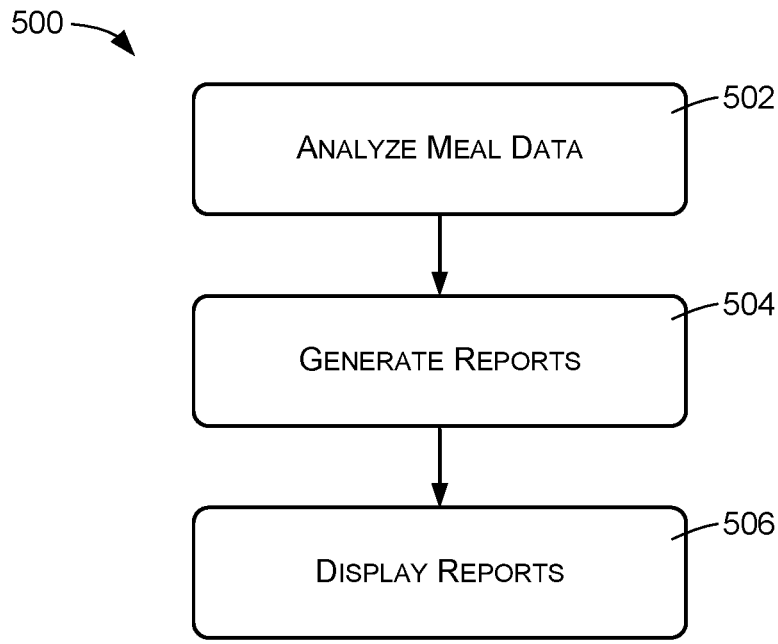
FIG. 5 is a flow diagram illustrating an example method of providing reports based at least in part on the meal data.

FIG. 5 shows an example method 500 that may be performed by the merchant support service 202 based at least in part on the meal data 414. The method 500 may, for example, be performed by the report engine 208 of the merchant support service 202 based on the meal data 414 received that has been created and stored by the method 400 of FIG. 4.

An action 502 comprises analyzing the meal data 414 to determine information such as ingredient freshness, the number of times particular containers have been accessed, the frequency of ingredient access for individual containers and their corresponding ingredients, relative popularities of different ingredient combinations, customer satisfaction, customer demographics, and so forth. An action 504 comprises generating reports, which may include information, indications, recommendations, and/or notifications, based on the meal analysis of the action 502. An action 506 comprises providing the reports, recommendations, and/or notifications to the restaurant, such as by displaying the recommendations, and/or notifications on the POS device 110, on other devices within the restaurant environment 100, and/or on other devices that may be used by restaurant employees such as smartphones and other personal devices.

While FIGS. 3-5 illustrate a general example of reporting based on video analysis, more specific examples will be described below. The examples below are based generally on analyzing the video 212 that is received contemporaneously with preparation and purchase of a customer meal. In the examples described herein, the results of the video analysis are indicated by the meal data 414, which contains detected operation attributes corresponding to each of multiple prepared and purchased meals. As described above, the operation attributes are for each customer meal, and may include things such as actions of food servers and customers during preparation of the meal, demographic information regarding customers, an identifier of a payment instrument used to purchase the meal, identities of food servers involved in customer interaction and in preparing the meal, explicit customer feedback for the meal, etc. In addition, the meal data 414 may include characterizations and/or classifications of actions, such as classifications of certain actions as being detrimental to customer satisfaction.

Figure 6:
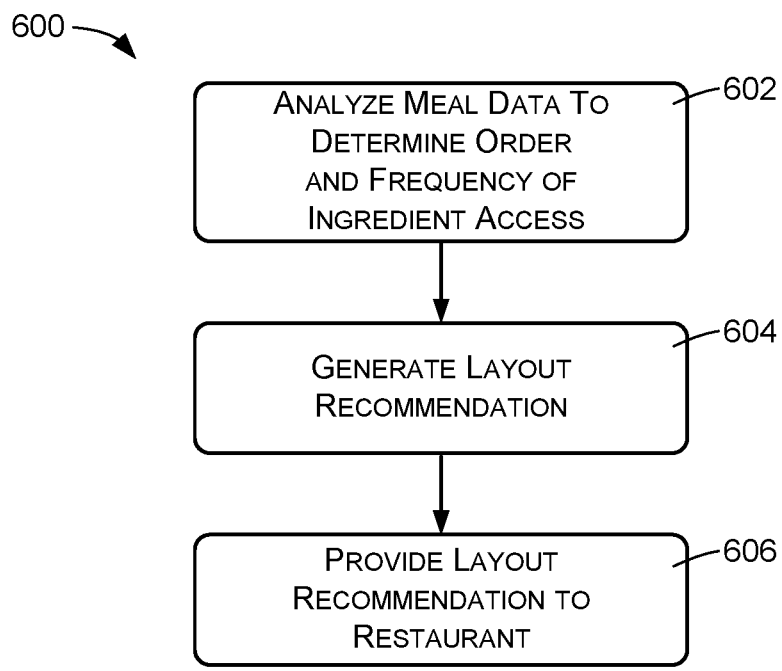
FIG. 6 is a flow diagram illustrating an example method of providing recommendations relating to the arrangement of food ingredients of a food service counter.

FIG. 6 shows a method 600 as an example of optimizing a customer-facing food service counter layout in a restaurant environment having a video recording system coupled to a merchant point-of-sale device or system. In this example, the merchant support service 202 analyzes the meal data 414 to recommend changes to the ingredient counter map 404, with the objective of increasing the speed of service provided by the food servers 108 and/or the speed or convenience with which the customer 106 may access the ingredient containers 104.

In the method 600, an action 602 may comprise analyzing the meal data 414 to determine the order and frequency of ingredient container access when preparing customer meals. An action 604 may comprise generating a recommendation regarding layout of the food service counter 102. More specifically, the action 604 may comprise determining one or more recommended modifications to the ingredient counter map 404 that will improve serving efficiency. An action 606 may comprise providing an indication to the restaurant, such as on the POS device 110, of the recommended modification to the ingredient counter map 404.

Figure 7:
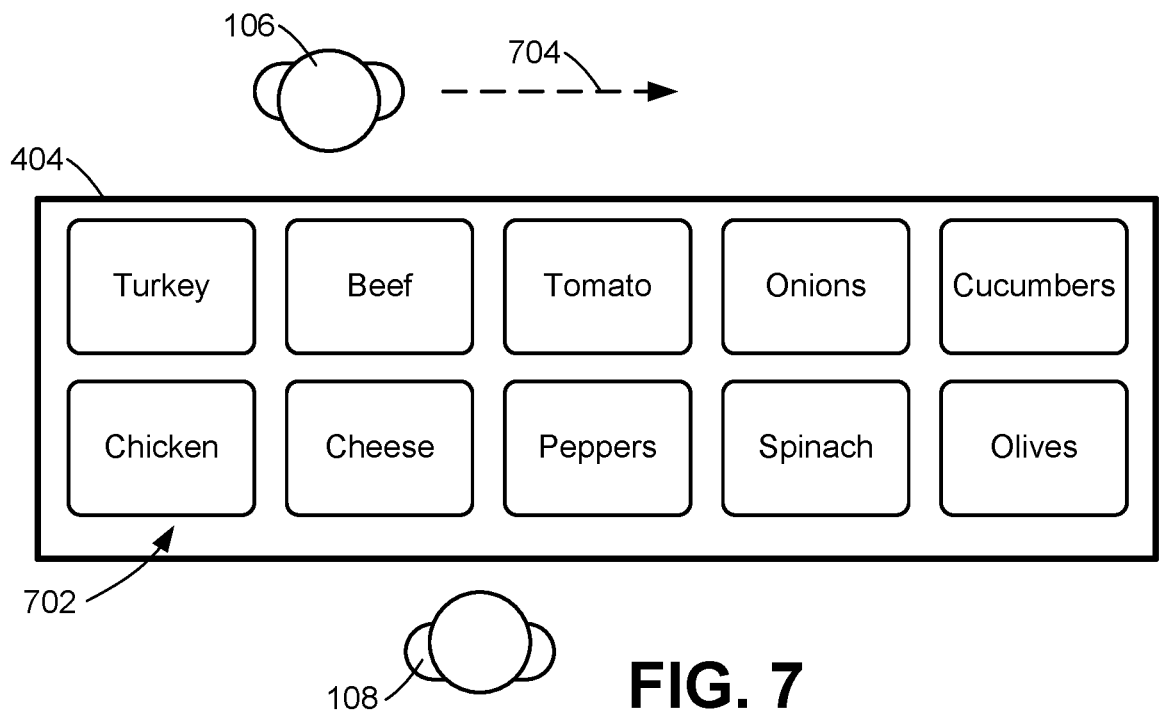
FIG. 7 is a visual representation of an ingredient counter map that specifies how ingredients are positioned relative to each other in a food service counter.

FIG. 7 shows a graphical example of an ingredient counter map 404 such as may be maintained by the merchant support service 202, having delineated ingredient areas 702 corresponding to the ingredient containers 104 of the food service counter 102. For directional reference, the customer 106 and a food server 108 are shown. It is assumed for purposes of discussion that the customer 106 will move along the food service counter from left to right as indicated by the dashed arrow 704.

In practice, the ingredient counter map 404 may be represented as a table or other data structure, in which ingredient areas 702 are represented by coordinates, and in which the ingredient areas 702 are associated with respectively named ingredients. As described above, the restaurant may supply the ingredient counter map 404 by interacting with a graphical user interface provided by the merchant support service 202.

Figure 8:
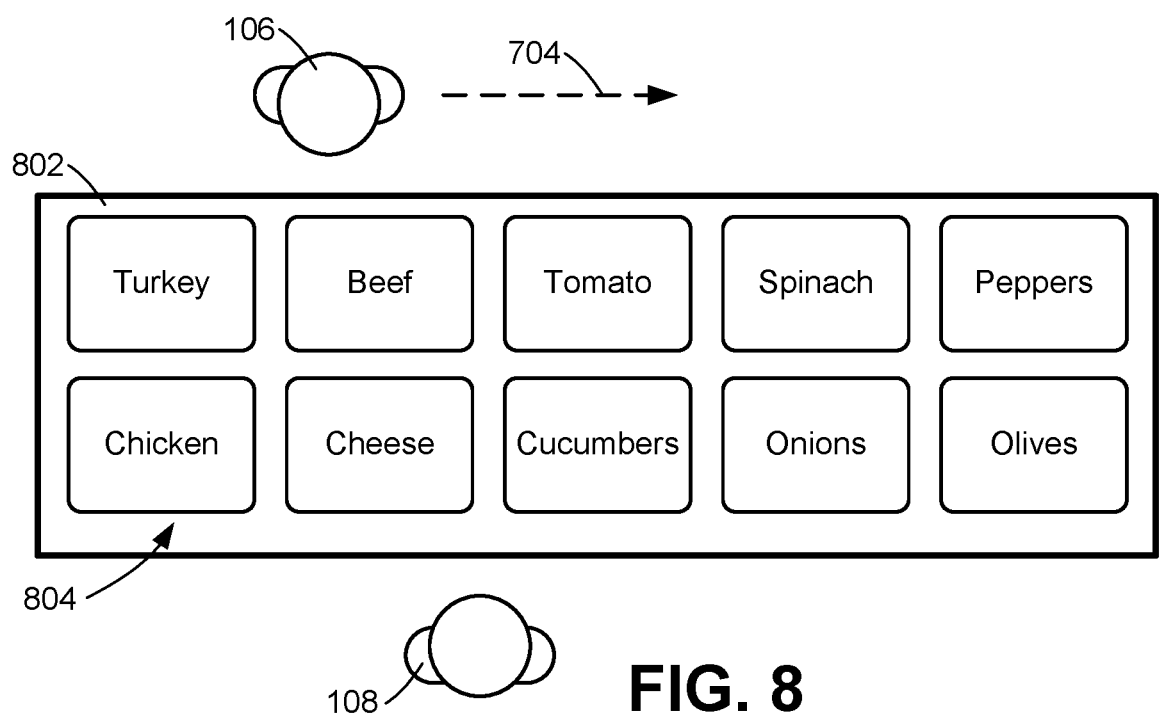
FIG. 8 is a visual representation of an ingredient counter map that has been modified to improve efficiencies and/or convenience of food servers and customers.

FIG. 8 shows a modified, recommended ingredient counter map 802 having ingredient areas 804 corresponding to the ingredient areas 702 of FIG. 7. In FIG. 8, however, the ingredients of the ingredient areas have been changed to show what has been determined to be a more optimal layout of the ingredients relative to each other and to the food service counter 102. Specifically, the positions of the spinach and onion ingredients have been swapped with each other, reflecting the hypothetical result, based on an analysis of the meal data 414, that onions are more frequently accessed than spinach, and therefore should be more accessible to the food servers 108. In addition, the positions of the cucumbers and peppers have been swapped with each other, reflecting the hypothetical result, based on an analysis of the meal data 414, that cucumbers are frequently accessed prior to accessing peppers, and therefore should be placed earlier along the food service counter 102 with respect to the typical direction of movement of the customer 106.

Graphics similar to the illustration of FIG. 8 may be shown on the POS device 102 as a recommendation regarding modifications to the counter layout that might improve serving efficiency, such as by increasing the speed or rate at which meals are assembled. In one example, the system can provide a calculated rate of speed increase based on an optimized layout and display the increased rate in conjunction with the recommended modified counter layout. For instance, the system may determine that the rate increase during hours for a particular day will be 40 customers per hour versus 30 customers due to popular ingredients during lunch being placed in closer proximity to the servers.

Recommendations for optimized counter layouts may be generated in different ways, based on the frequency with which ingredients are used, the order in which they are used, the number of available servers, preferred assembly sequences, and other factors. When multiple food servers are present, for example, the layout may be optimized to distribute work evenly between the multiple food servers. When assembly starts with certain ingredients, those ingredients may be placed earlier along the food service counter 102. More frequently accessed ingredients may be positioned nearer the servers.

Figure 9:
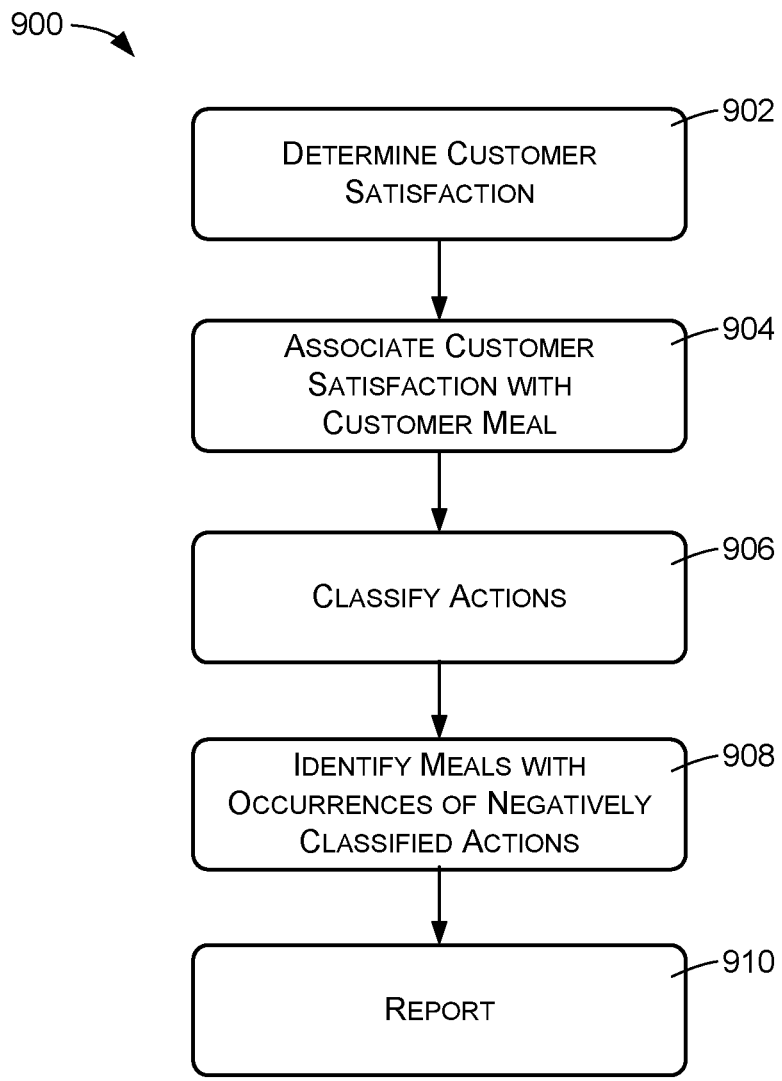
FIG. 9 is a flow diagram illustrating an example method of providing reports relating to actions of food servers that may negatively affect customer satisfaction.

FIG. 9 shows a method 900 as another example of analyzing food service counter operations and of providing reports to the restaurant. In this example, the merchant support service 202 provides reports regarding interactions between customers and food servers, including reports regarding specific actions performed by specific food servers that may have impacted reported levels of customer satisfaction.

An action 902 may comprise determining a level of customer satisfaction for a particular meal. For example, in some embodiments the merchant support service 202 may receive explicit customer feedback regarding a purchased meal. In particular, in some embodiments the merchant support service 202 may be configured to provide electronic receipts to purchasing customers after completing purchase transactions, where the electronic receipts solicit ratings or evaluations of purchased meals. More specifically, during a transaction a customer may provide an email address, which is in turn provided to the merchant support service 202 as part of the transaction information. Upon completing the purchase transaction, the payment processing component 204 may send a receipt for the purchase transaction to the provided email address of the customer. The receipt may provide hyperlinks to online forms or web pages that allow the customer to provide ratings or evaluations of transactions. For example, an email containing a transaction receipt may also include a link to a website where a customer may provide a simple rating for the transaction and/or the products involved in the transaction. Alternatively, the email itself may have graphical elements that can be selected to provide product/service ratings. A graphical element corresponding to a "4-star" rating, for example, may be associated with a hyperlink that effectively communicates the rating to the payment processing component 204. Ratings may use any appropriate scale, such as good/fair/bad, 1-10, 1-5 stars, etc. Other forms of electronic communications may also be used for this purpose, such as text messaging, social network messaging, etc.

As another example, the action 902 may comprise analyzing the video 212 and/or the previously collected meal data 414 in order to evaluate a level of satisfaction of the customer for a purchased meal. More specifically, the action 902 may comprise evaluating customer-related attributes such as customer facial expressions and/or vocal utterances in order to determine levels of customer satisfaction as the customer selects food ingredients.

An action 904 may comprise associating a reported or evaluated level of customer satisfaction with the meal data 414 for a specific meal. More generally, as customer satisfaction for each meal is determined, previously stored meal data 414 for that meal may be supplemented to include an evaluated level of customer satisfaction.

An action 906 may comprise classifying observed actions of the food servers 108 as to whether they are consistently associated with either high or low customer satisfaction. The action 906 may comprise analyzing the meal data 414 to determine which types of observed actions contribute to customer satisfaction or dissatisfaction. For example, customer meals for which the meal data 414 indicates that a particular food server action occurred may be identified, and an average customer feedback score or customer satisfaction level for those customer meals may be calculated. Average scores or levels for meals during which different observed food server actions occurred may be compared. Lower scores or levels may indicate that certain observed actions are detrimental to customer satisfaction. Higher scores or levels may indicate that certain other observed actions contribute positively to customer satisfaction.

An action 908 may comprise identifying meals for which the meal data 414 indicates that one or more detrimental actions occurred, where the detrimental actions are those identified in the action 906 as being detrimental to customer satisfaction. For example, the action 908 may comprise analyzing the meal data 414 to identify a particular transaction that received negative customer feedback and during which a negatively classified action was performed by a particular food server 108. The action 908 may further comprise identifying the food server 108 who performed the negatively classified action, based again on the meal data 414. In some cases, the action 908 may comprise identifying food servers who perform detrimental actions relatively large numbers of times.

An action 910 may comprise providing a report to the restaurant that identifies the one or more food servers who have performed detrimental actions, as well as identifying the specific detrimental actions that were performed by each food server. A report such as this may be provided periodically, such as by displaying the report on the POS device 110, in order to coach restaurant employees and to improve customer service. Reports may similarly be provided that identify food servers who contribute to positive customer feedback. In some embodiments, the action 910 may comprise reporting evaluated customer satisfaction for multiple customer meals that have been prepared at least in part by a particular identified food server or for multiple food servers. In some cases, the action 910 may report only meals that were evaluated as producing low customer satisfaction, and may identify the food servers and/or actions performed by the food servers that may have contributed to the low customer satisfaction. In some cases, the action 910 may report only meals that were evaluated as producing relatively high customer satisfaction, and may identify the food servers and/or actions performed by the food servers that may have contributed to the high customer satisfaction.

Figure 10:
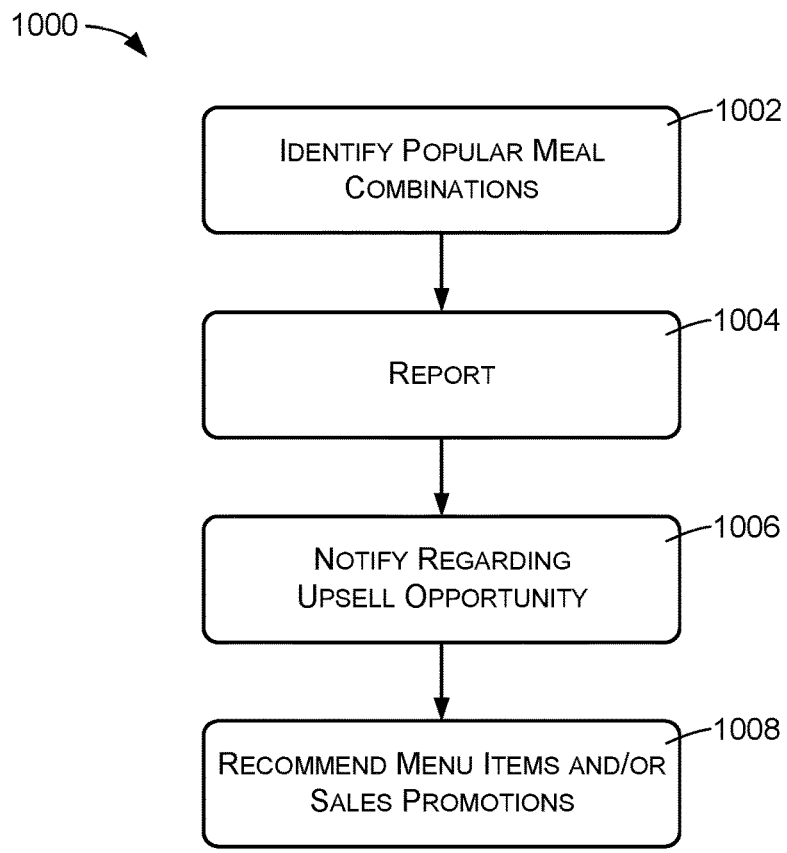
FIG. 10 is a flow diagram illustrating an example method of recommending new menu items and/or sales promotions based on the evaluated popularity of different ingredient combinations.

FIG. 10 shows a method 1000 as another example of analyzing food service counter operations and of providing reports. In this example, an action 1002 may comprise analyzing the meal data 414 to determine popular ingredient combinations corresponding to different menu items. For example, the action 1102 may comprise analyzing multiple meals represented by the meal data and identifying unique ingredient combinations that are frequently selected and used to create a customer meal.

An action 1004 may comprise reporting to the restaurant, such as on the POS device 110 of the restaurant, the popular ingredient combinations of the customer meals. The restaurant may find this information useful in deciding upon new menu items and/or for providing sales promotions. For example, the restaurant may decide to offer a discount or other promotion for meals having certain ingredient combinations. In some embodiments, the action 1004 may report popular ingredient combinations for different demographic groups, based on the demographic information contained in the meal data 414. Information such as this may be useful to the restaurant when determining various types of promotional events or offerings.

In some embodiments, an action 1006 may be performed, comprising notifying the restaurant, based on the meal ingredients of a meal currently being purchased by a customer, of the opportunity to recommend another menu item to the customer as an upsell. For example, analysis of the meal data 414 may reveal that customers who have selected a particular combination of ingredients frequently purchase a particular additional menu item, and a notice may be provided on the POS device 110 for the service person 112 to suggest this additional menu item.

In some embodiments, an action 1008 may be performed, comprising providing one or more recommendations to the restaurant regarding menu items and/or promotions. For example, a recommendation may be provided for the addition of a menu item for a meal containing one of the popular ingredient combinations. Similarly, a recommendation may be provided for one or more sales promotions for meals comprising popular ingredient combinations.

Figure 11:
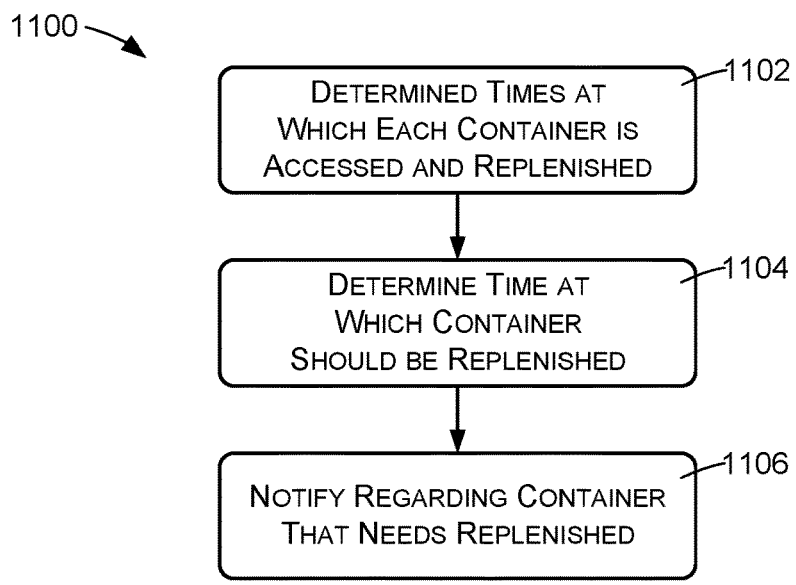
FIG. 11 is a flow diagram illustrating an example method of providing notifications that certain ingredients need to be replenished.

FIG. 11 shows a method 1100 as another example of analyzing food service counter operations and of providing reports to the restaurant. In this example, an action 1102 may comprise analyzing the meal data 414 and recording the number of times that each food container is accessed and the times at which different ingredients are replenished. Ingredient replenishment may comprise adding more of the ingredient to its ingredient container 104 or replacing the ingredients of the container with fresh ingredients. In some cases, replenishment may involve preparation such as chopping, grating, cooking, etc.

An action 1104 may comprise determining, based at least in part on the number of times that a particular ingredient container has been accessed since it was last replenished, a time at which the particular ingredient container needs to be again replenished. An action 1106 may comprise providing a notification to the restaurant, such as by displaying a notice or other indication on the POS device 110, that an action needs to be taken with respect to the ingredient held by the particular ingredient container. For example, the action 1106 may comprise notifying the restaurant staff that the ingredient needs to be replenished.

Figure 12:
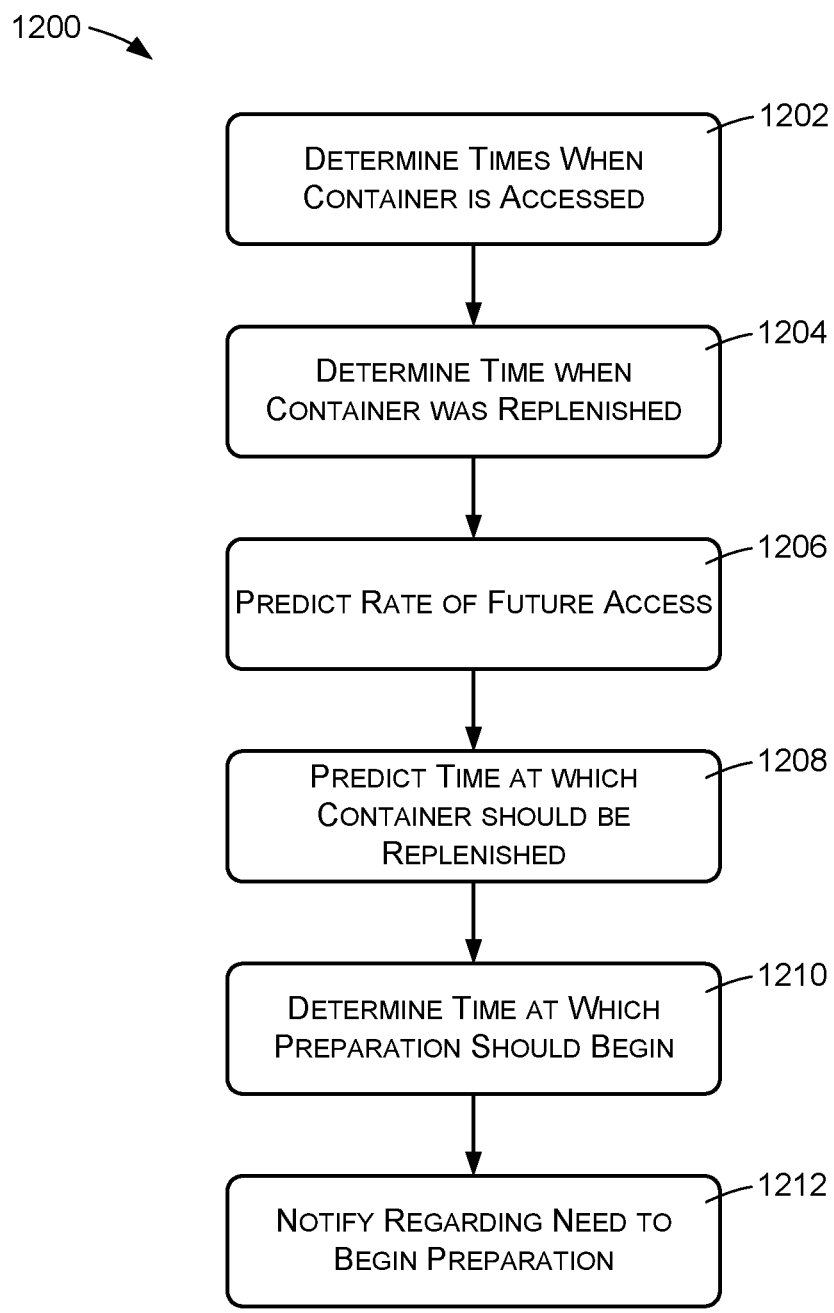
FIG. 12 is a flow diagram illustrating another example method of providing notifications that certain ingredients need to be replenished.

FIG. 12 shows a method 1200 as another example of analyzing food service counter operations and of providing reports, recommendations, and/or notifications to the restaurant. In this example, an action 1202 may comprise analyzing the meal data 414 to determine the times at which a particular ingredient container is or has been accessed. An action 1204 may comprise determining the time at which a particular ingredient container, holding a particular ingredient, was last replenished. The action 1204 may be performed, for example, by receiving input from a restaurant employee via the POS device 110 or by detecting analyzing the meal data 414.

An action 1206 may comprise predicting a rate of future access of the particular ingredient container, based at least in part on the recorded times. For example, the previously determined times that the container was accessed may be analyzed to determine frequency of access to the container during different times of the day and/or different times of the week, and from that analysis may be predicted the upcoming demand for each ingredient.

An action 1208 may comprise predicting, based at least in part on the predicted rate of future access to the container, a time at which the ingredient container should be replenished. An action 1210 may comprise determining, based at least in part on a known preparation time of the ingredient held by the container and the predicted time at which the particular ingredient will be depleted, a time at which preparation of the particular ingredient should begin. An action 1212 may comprise, at or before the time at which the preparation of the particular ingredient should begin, providing a notification on the POS device that the ingredient container needs to be replenished and/or that preparation of the ingredient should begin.

FIG. 13 shows a method 1300 as another example of analyzing food service counter operations and of providing reports, recommendations, and/or notifications to the restaurant. In this example, an action 1302 may comprise analyzing the meal data 414 to determine or record the time at which a particular ingredient container, holding a particular ingredient, was last replenished. The action 1302 may be performed, for example, by receiving input from a restaurant employee via the POS device 110 or by detecting a replenishment event by analyzing the received video.

An action 1304 may comprise further analyzing the meal data 414 to determine, based on the time of the last replenishment, that the ingredient held by the particular ingredient container has exceeded a freshness period. A freshness period, for example, might comprise a number of minutes following the time of the last replenishment. An action 1306 may then be performed of notifying the restaurant that an action needs to be taken with respect to the ingredient, such as replacing the ingredient. The action 1306 may in some cases be performed at an time that accounts for preparation time of the ingredient, as described above with reference to FIG. 12.

FIG. 14 shows an example of a POS device 110 that may be used in the environment described herein. Generally, POS device 110 may comprise any type of computerized device that has or can be associated with a graphical display upon which visual content can be shown. Examples of such devices include personal computers, smartphones, tablet computers, laptop computers, projection systems, television systems, and so forth.

In the illustrated example, the POS device 110 includes at least one processor 1402 and associated memory 1404. Each processor 1402 may itself comprise one or more processors or processing cores. For example, the processor 1402 can be implemented as one or more microprocessors, microcomputers, microcontrollers, digital signal processors, central processing units, state machines, logic circuitries, and/or any devices that manipulate signals based on operational instructions. In some cases, the processor 1402 may be one or more hardware processors and/or logic circuits of any suitable type specifically programmed or configured to execute the algorithms and processes described herein. The processor 1402 can be configured to fetch and execute computer-readable processor-executable instructions stored in the memory 1404.

Depending on the configuration of the POS device 110, the memory 1404 may be an example of tangible non-transitory computer storage media and may include volatile and nonvolatile memory and/or removable and non-removable media implemented in any type of technology for storage of information such as computer-readable processor-executable instructions, data structures, program modules or other data. The memory 1404 may include, but is not limited to, RAM, ROM, EEPROM, flash memory, solid-state storage, magnetic disk storage, optical storage, and/or other computer-readable media technology. Further, in some cases, the POS device 110 may access external storage, such as RAID storage systems, storage arrays, network attached storage, storage area networks, cloud storage, or any other medium that can be used to store information and that can be accessed by the processor 1402 directly or through another computing device or network. Accordingly, the memory 1404 may be computer storage media able to store instructions, modules or components that may be executed by the processor 1402. Further, when mentioned, non-transitory computer-readable media exclude media such as energy, carrier signals, electromagnetic waves, and signals per se.

The memory 1404 may be used to store and maintain any number of functional components that are executable by the processor 1402. In some implementations, these functional components comprise instructions or programs that are executable by the processor 1402 and that, when executed, implement operational logic for performing the actions and services attributed above to the POS device 110.

In the context of the examples described above, functional components of the POS device 110 stored in the memory 1404 may include an operating system 1406 for controlling and managing various functions of the POS device 110. The memory 1404 may also store one or more applications 1408, such as may be used to provide POS functionality and/or to expose the POS functionality enabled by the merchant support service 202. The memory 1404 may also store additional data, data structures, and the like, not shown, that are used in the course of operations of the POS device 110 and its components.

The POS device 110 may have or be associated with a display component 1410 upon which received content is displayed. The display component 1410 may be integral to the POS device 110 or may be connected to or otherwise associated with the POS device 110.

The POS device 110 may have various input components 1412, which may include a keyboard, a mouse, a stylus, a touch screen, etc. One or more of the input components may be used to perform selection of control elements within displayed content.

The POS device 110 may have a network communications interface 1414, such as an Ethernet communications interface, which provides communication by the POS device 110 with various network-based or Internet-based servers, including the merchant support service 202.

The POS device 110 may of course include many other logical, programmatic, and physical components that are not specifically described herein.

FIG. 15 shows an example of one of the server computers 1500 that may be used to implement the merchant support service 202. In the illustrated example, each server computer 1500 includes at least one processor 1502 and associated memory 1504. Each processor 1502 may itself comprise one or more processors or processing cores. For example, the processor 1502 can be implemented as one or more microprocessors, microcomputers, microcontrollers, digital signal processors, central processing units, state machines, logic circuitries, and/or any devices that manipulate signals based on operational instructions. In some cases, the processor 1502 may be one or more hardware processors and/or logic circuits of any suitable type specifically programmed or configured to execute the algorithms and processes described herein. The processor 1502 can be configured to fetch and execute computer-readable processor-executable instructions stored in the memory 1504.

Depending on the configuration of the server computer 1500, the memory 1504 may be an example of tangible non-transitory computer storage media and may include volatile and nonvolatile memory and/or removable and non-removable media implemented in any type of technology for storage of information such as computer-readable processor-executable instructions, data structures, program modules or other data. The memory 1504 may include, but is not limited to, RAM, ROM, EEPROM, flash memory, solid-state storage, magnetic disk storage, optical storage, and/or other computer-readable media technology. Further, in some cases, the server computer 1500 may access external storage, such as RAID storage systems, storage arrays, network attached storage, storage area networks, cloud storage, or any other medium that can be used to store information and that can be accessed by the processor 1502 directly or through another computing device or network. Accordingly, the memory 1504 may be computer storage media able to store instructions, modules or components that may be executed by the processor 1502. Further, when mentioned, non-transitory computer-readable media exclude media such as energy, carrier signals, electromagnetic waves, and signals per se.

The memory 1504 may be used to store and maintain any number of functional components that are executable by the processor 1502. In some implementations, these functional components comprise instructions or programs that are executable by the processor 1502 and that, when executed, implement operational logic for performing the actions and services attributed above to the merchant support service 202.

In the context of the examples described above, functional components of the server 1500 stored in the memory 1504 may include an operating system 1506 for controlling and managing various functions of the server 1500. The memory 1504 may also store a web services component 1508. The web services component 1508 is responsible for receiving content requests from various networked client devices and providing content in response to such requests. The memory 1504 may also store various applications 1510 that implement the merchant service functionality described herein. The applications 1510 may include, for example the payment processing component 204, the video analysis component 206, and the report engine 208.

The server 1500 may have a network communications interface 1512, such as an Ethernet communications interface, which provides communication by the server 1500 with other servers and with client devices such as the POS device 110.

The server 1500 may of course include many other logical, programmatic, and physical components that are not specifically described herein.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. A method comprising:
   receiving, by one or more service computing devices associated with a merchant support service and via an information capturing device, information regarding a food service counter maintained by a merchant, wherein the food service counter has ingredient containers that hold available ingredients for viewing and selection by a customer, each ingredient container holding an available ingredient;
   analyzing, by the one or more service computing devices, the information received via the information capturing device to identify ingredient containers that are accessed to prepare a customer meal, wherein analyzing the information comprises at least one of image recognition, text recognition, or audio detection;
   identifying, by the one or more service computing devices and based on analyzing the information received via the information capturing device, meal ingredients of the customer meal, the meal ingredients comprising the available ingredients corresponding respectively to the ingredient containers that have been accessed;
   analyzing, by the one or more service computing devices, additional meal ingredients used in a plurality of customer meals associated with a plurality of customers of the merchant;
   generating, by the one or more service computing devices and based at least in part on analyzing the additional meal ingredients, one or more reports regarding the food service counter, wherein the one or more reports comprise at least one of a recommended layout of the available ingredients, an indication of customer satisfaction, or an indication of an action corresponding to at least one of the available ingredients; and
   causing, by the one or more service computing devices, an interface of a merchant device to display the one or more reports to the merchant.

2. The method of claim 1, wherein:
   the available ingredients have a first layout that indicates first locations of the available ingredients; and
   wherein the one or more reports further comprise a recommendation of a second layout of the available ingredients.

3. The method of claim 1, further comprising:
   further analyzing the additional meal ingredients used in the plurality of the customer meals to determine popular ingredient combinations; and
   wherein the one or more reports further comprise an indication of the popular ingredient combinations.

4. The method of claim 3, wherein the one or more reports further comprise a recommendation of a sales promotion for a menu item comprising at least one of the popular ingredient combinations.

5. The method of claim 3, wherein the one or more reports recommend addition of a menu item for a meal containing one of the popular ingredient combinations.

6. The method of claim 1, further comprising:
   identifying an additional menu item based at least in part on the meal ingredients of the customer meal; and
   wherein the one or more reports further comprise a recommendation of the additional menu item as an upsell for the customer.

7. The method of claim 1, further comprising:
   recording a number of times that a particular ingredient container is accessed;
   determining, based at least in part on the number of times that the particular ingredient container is accessed, that the particular ingredient container needs to be replenished; and
   wherein the one or more reports comprise the indication of the action corresponding to the at least one of the available ingredients, and wherein the indication of the action comprises a notification that the particular ingredient container needs to be replenished.

8. The method of claim 1, further comprising:
   further analyzing the information received via the information capturing device to determine a time at which a particular ingredient container was last replenished;
   determining, based on the time, that the ingredient held by the particular ingredient container has exceeded a freshness period; and
   wherein the one or more reports comprise the indication of the action corresponding to the at least one of the available ingredients, and wherein the action needs to be taken with respect to the ingredient held by the particular ingredient container.

9. The method of claim 1, further comprising:
   recording times at which a particular ingredient container is accessed;
   predicting a rate of future access of the particular ingredient container based at least in part on the recorded times;
   predicting, based at least in part on the predicted rate of future access, a first time at which the particular ingredient container should be replenished;
   determining, based at least in part on a known preparation time of a first ingredient held by the particular ingredient container, a second time before which preparation of the first ingredient should begin; and
   wherein the one or more reports comprise the indication of the action corresponding to the at least one of the available ingredients, and wherein the indication of the action comprises a notification that preparation of the first ingredient should begin.

10. The method of claim 1, further comprising:
    analyzing the information received via the information capturing device to identify one or more demographic characteristics of the customer who purchased the customer meal;
    analyzing the additional meal ingredients used in the plurality of customer meals purchased by a subset of customer of the plurality of customers having a particular demographic characteristic to identify a particular combination of meal ingredients that is relatively popular with the subset of the customers; and
    wherein the one or more reports further comprise an indication that the particular combination of meal ingredients is relatively popular with the subset of the customers.

11. The method of claim 1, further comprising:
analyzing the information received via the information capturing device to evaluate satisfaction of the customer who purchased the customer meal;
analyzing the from the information capturing device to identify a food server who participated in preparing the customer meal; and
wherein the one or more reports comprise the indication of customer satisfaction for a portion of the plurality of the customer meals prepared at least in part by the food server.

12. The method of claim 1, further comprising:
analyzing the information received via the information capturing device to identify one or more actions of one or more food servers who access the ingredient containers to assemble the customer meal;
receiving first customer feedback from the customer;
analyzing a plurality of actions and second customer feedback for the plurality of customer meals to determine one or more food server actions that correspond to negative customer feedback; and
wherein the indication of customer satisfaction includes the one or more food server actions that correspond to the negative customer feedback.

13. The method of claim 1, further comprising:
analyzing the information received via the information capturing device to (a) identify a particular food server who accessed at least one of the ingredient containers and (b) detect at least one action performed by the particular food server, the one or more actions being detrimental to the customer satisfaction; and
wherein the one or more reports comprise the indication of the action corresponding to the at least one of the available ingredients and further include an indication of the particular food server, and wherein the action corresponds to the at least one action that was detrimental to customer satisfaction.

14. A system for optimizing a food service counter layout in a restaurant environment having an information recording system, the system, comprising:
one or more processors;
one or more non-transitory computer-readable media storing instructions executable by the one or more processors, wherein the instructions program the one or more processors to perform actions comprising:
receiving, by one or more service computing devices associated with a merchant support service and via the information recording system, information of a food service counter maintained by a merchant, wherein the food service counter has ingredient containers that hold available ingredients for viewing and selection by a customer of the merchant;
analyzing, by the one or more service computing devices, the information received via the information recording system to identify meal ingredients used to assemble individual customer meals of a plurality of customer meals associated with a plurality of customers of the merchant, wherein analyzing the information comprises at least one of image recognition, text recognition, or audio detection;
generating, by the one or more service computing devices and based at least in part on the analyzing, one or more reports regarding the food service counter; and
causing, by the one or more service computing devices, an interface of a merchant point-of-sale (POS) system to display the one or more reports.

15. The system of claim 14, the actions further comprising:
determining popular ingredient combinations based at least in part on the meal ingredients used to assemble the individual customer meals of the plurality of customer meals; and
wherein the one or more reports indicate the popular ingredient combinations.

16. The system of claim 15, wherein the one or more reports recommend a sales promotion for a meal comprising one or more of the popular ingredient combinations.

17. The system of claim 15, wherein the one or more reports recommend a new menu item for a meal containing one of the popular ingredient combinations.

18. The system of claim 14, wherein the available ingredients have a first layout that indicates first locations of the available ingredients, and wherein the one or more reports recommend a second layout.

19. One or more non-transitory computer-readable media storing instructions executable by one or more processors that, when executed by the one or more processors, cause the one or more processors to perform acts comprising:
receiving, by one or more service computing devices associated with a merchant support service and via an information capturing device, information regarding a food service counter maintained by a merchant, wherein the food service counter has ingredient containers that hold available ingredients for viewing and selection by a customer, each ingredient container holding an available ingredient;
analyzing, by the one or more service computing devices, the information received via the information capturing device to identify ingredient containers that are accessed to prepare a customer meal, wherein analyzing the information comprises at least one of image recognition, text recognition, or audio detection;
identifying, by the one or more service computing devices and based on analyzing the information received via the information capturing device, meal ingredients of the customer meal, the meal ingredients comprising the available ingredients corresponding respectively to the ingredient containers that have been accessed;
analyzing, by the one or more service computing devices, additional meal ingredients used in a plurality of customer meals associated with a plurality of customers of the merchant;
generating, by the one or more service computing devices and based at least in part on analyzing the additional meal ingredients, one or more reports regarding the food service counter, wherein the one or more reports comprise at least one of a recommended layout of the available ingredients, an indication of customer satisfaction, or an indication of an action corresponding to at least one of the available ingredients; and
causing, by the one or more service computing devices, an interface of a merchant device to display the one or more reports to the merchant.

20. The one or more non-transitory computer-readable media as claim 19 recites, the acts further comprising:
identifying an additional menu item based at least in part on the meal ingredients of the customer meal; and
wherein the one or more reports recommend the additional menu item as an upsell for the customer.

21. The one or more non-transitory computer-readable media as claim 19 recites, wherein:
the available ingredients have a first layout that indicates first locations of the available ingredients; and the one or more reports further comprise a recommendation of a second layout.

22. The one or more non-transitory computer-readable media as claim 19 recites, the acts further comprising:
analyzing the meal ingredients of the plurality of customer meals to determine popular ingredient combinations; and
wherein the one or more reports further comprise an indication of the popular ingredient combinations.

23. The one or more non-transitory computer-readable media as claim 22 recites, wherein the one or more reports further comprise a recommendation of a sales promotion for a menu item comprising at least one of the popular ingredient combinations.

24. The one or more non-transitory computer-readable media as claim 22 recites, wherein the one or more reports further comprise a recommendation that the merchant add a menu item corresponding to a meal comprising at least one of the popular ingredient combinations.

* * * * *